(12) United States Patent
Pilvísto et al.

(10) Patent No.: US 7,846,090 B2
(45) Date of Patent: Dec. 7, 2010

(54) ENDOSCOPE

(75) Inventors: Tonis Pilvísto, Tallinn (EE); Viktor Josef Wimmer, Seeon (DE)

(73) Assignee: Karl Storz GmbH & Co. KG (DE)

( * ) Notice: Subject to any disclaimer, the term of this patent is extended or adjusted under 35 U.S.C. 154(b) by 937 days.

(21) Appl. No.: 11/513,811

(22) Filed: Aug. 31, 2006

(65) Prior Publication Data

US 2007/0099500 A1 May 3, 2007

(30) Foreign Application Priority Data

Aug. 31, 2005 (DE) .................. 10 2005 041 454

(51) Int. Cl.
*A61B 1/00* (2006.01)
*A61B 1/04* (2006.01)

(52) U.S. Cl. .................. 600/153; 600/107; 600/149

(58) Field of Classification Search .................. 600/153, 600/104, 149, 173, 106, 107, 157, 136, 147, 600/146, 145, 148, 150; 403/21; 439/263, 439/820, 821; 279/48, 32, 53

See application file for complete search history.

(56) References Cited

U.S. PATENT DOCUMENTS

| | | | | |
|---|---|---|---|---|
| 1,854,782 A | * | 4/1932 | Cook | 439/788 |
| 2,014,056 A | * | 9/1935 | Van Noorden | 439/820 |
| 2,063,718 A | * | 12/1936 | Berndt | 439/788 |
| 2,100,272 A | * | 11/1937 | Sawyer | 476/15 |
| 2,560,947 A | * | 7/1951 | Greenberg | 279/32 |
| 4,189,203 A | * | 2/1980 | Miller | 439/263 |
| 5,299,559 A | * | 4/1994 | Bruce et al. | 600/141 |
| 5,707,344 A | | 1/1998 | Nakazawa et al. | 600/127 |
| 6,699,183 B1 | * | 3/2004 | Wimmer | 600/147 |
| 2001/0044570 A1 | | 11/2001 | Ouchi et al. | 600/107 |
| 2004/0186429 A1 | * | 9/2004 | Owens et al. | 604/117 |

FOREIGN PATENT DOCUMENTS

| | | |
|---|---|---|
| DE | 196 27 016 | 2/1998 |
| EP | 0 609 503 | 8/1994 |
| EP | 1 112 019 B1 | 7/2001 |
| WO | WO 0013569 A1 * | 3/2000 |

OTHER PUBLICATIONS

European Search Report, Mar. 8, 2007, 4 pages.

* cited by examiner

*Primary Examiner*—Linda C Dvorak
*Assistant Examiner*—Alireza Nia
(74) *Attorney, Agent, or Firm*—St. Onge Steward Johnston & Reens LLC

(57) ABSTRACT

The invention relates to an endoscope having a shaft in which at least one working channel is positioned and having on the distal end of the shaft an endoscope head, such that the part of the working channel contained in the endoscope head can be rotated with respect to the related working channel by a Bowden cable that is mounted on a control handle on the proximal end by a collet. To configure an endoscope in such a manner that it ensures simple construction as well as a constantly even tension of the Bowden cable, it is proposed with the invention that the depth of insertion of a cable cord of the Bowden cable into the collet can be limited by a pressure element acting on the cable cord and collet.

12 Claims, 4 Drawing Sheets

Fig. 1
Fig. 7
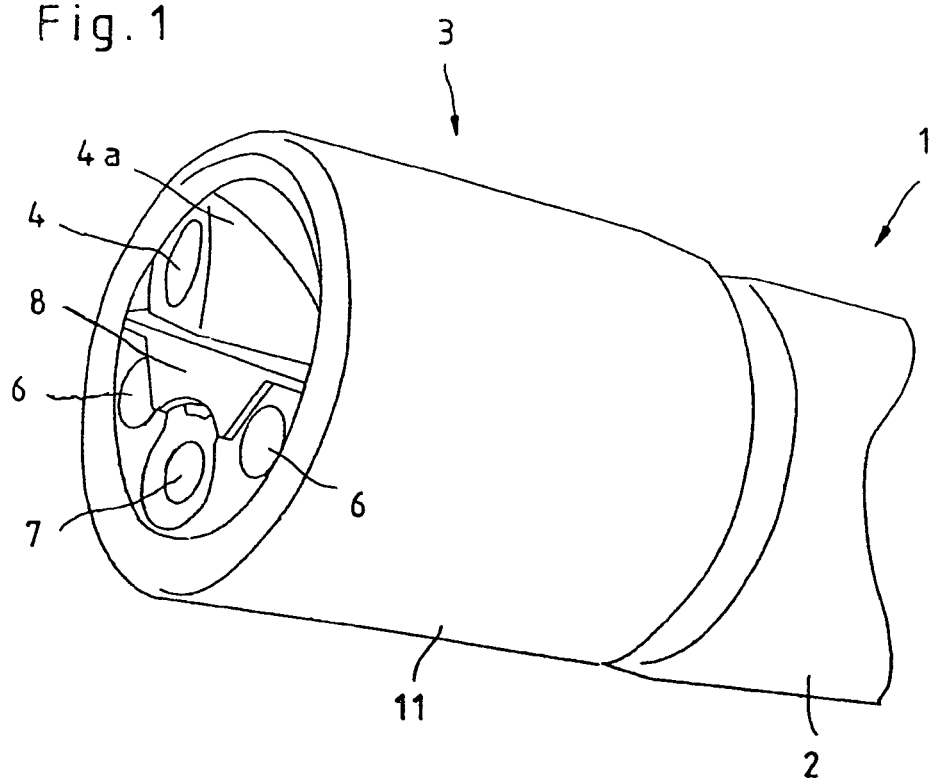
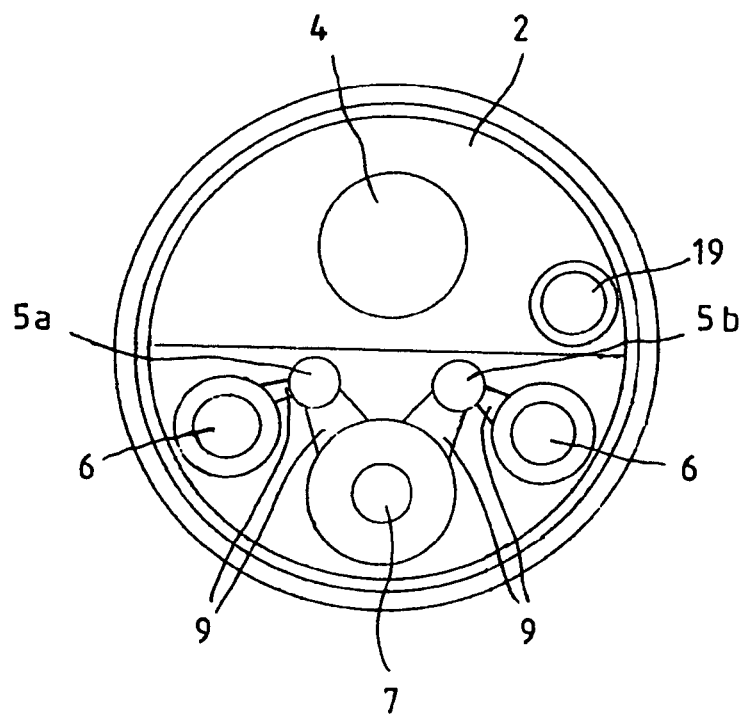

ENDOSCOPE

CROSS-REFERENCE TO RELATED APPLICATIONS

The present application claims priority of German patent application No. 10 2005 041 454.0 filed on Aug. 31, 2005, the content of which is incorporated herein by reference.

FIELD OF THE INVENTION

The invention relates to an endoscope having a shaft in which at least one working channel is positioned and having on the distal end of the shaft an endoscope head, such that the part of the working channel contained in the endoscope head can be rotated with respect to the related working channel by a Bowden cable that is mounted on a control handle on the proximal end by a collet.

BACKGROUND OF THE INVENTION

In order to allow a medical instrument brought into the surgical area by way of the working channel to be directed accurately to the area of application, a known method is to configure the part of the working channel situated in the endoscope head so that it can be rotated with respect to the related working channel by means of a Bowden cable. In the endoscope introduced in EP 1 112 019 B1, the Bowden cable serving to rotate the working channel is mounted on the proximal end by means of a collet mounted on a control handle. By means of the collet, the cable cord of the Bowden cable is grasped by clamping and is held clamped in the collet according to the depth of insertion.

This known construction for clamping the Bowden cable has the disadvantage that the cable cord can be inserted so deep in the collet that the cable cord becomes too taut and it becomes scarcely possible to rotate the working channel. To minimize this danger, the working channel and thus the cable cord of the Bowden cable must first be moved into a predetermined starting position so that thereafter a sufficient but not too taut tightening of the cable cord by the collet is possible. This known clamping method is, on the one hand, complicated and, on the other hand, does not prevent faulty tightening of the cable cord.

On this basis, it is the object of the invention to produce an endoscope of the aforementioned type in such a way that a constantly even tension of the Bowden cable is ensured, along with simple construction.

SUMMARY OF THE INVENTION

The fulfillment of this object according to the invention is characterized in that the depth of insertion of a cable cord of the Bowden cable into the collet can be limited by a pressure element applied to the cable cord and collet.

Because the invention limits the depth of insertion of the cable cord of the Bowden into the collet, it becomes possible for the first time to maintain constant uniform depth of insertion and thus also a uniform tension of the cable cord. The risk of faulty tightening of the cable cord in assembling the Bowden cable is avoided thanks to this structural design.

According to a practical embodiment of the invention it is proposed that a cone is configured on the proximal end of the collet so that it engages with a counter-cone that is configured in a nut that can be screwed onto the collet. The engagement of cone and counter-cone ensures a secure and straight mounting of the collet in the nut, so that in the cone of the collet at least one clamping slit is configured running in the longitudinal direction of the collet whereby the cable cord is fixed in the collet by clamping when the collet cone runs up against the counter-cone.

To ensure that the counter-cone is always form-fitting contiguous to the cone of the collet, the pressure element according to the invention acts on the counter-cone by means of at least one spring element.

In addition, according to a preferred embodiment of the invention it is proposed that the pressure element is configured as a cap-shaped component, so that the axial length of the pressure element corresponds to the preferred and maximal insertion depth of the cable cord into the collet. Because the cap-shaped pressure element is spring-loaded and contiguous with the counter-cone, which defines the final position of the collet in the nut, there results an always uniform and predetermined tightening of the cable cord, because upon screwing the nut onto the collet positioned coaxially on the cable cord, the cable cord on the proximal end, corresponding only to the axial length of the pressure element, can extend above the collet. Thus, in installing the Bowden cable on the control handle, the insertion depth of the cable cord is restricted by the pressure element.

It is further proposed with the invention that the spring element is supported on the distal end on a surrounding collar of the cap-shaped pressure element and on the proximal end on a rear wall of the nut that is configured as a cap nut.

To ensure that the cable cord of the Bowden cable is always perfectly centered in the pressure element, it is proposed with the invention that a closed rear wall of the cap-shaped pressure element is configured tapering toward the outside.

It is finally proposed with the invention that the counter-cone is configured on a sleeve that can be inserted into the nut, so that the sleeve can be fixed secure against rotation in the nut, for instance by cementing, in order to prevent turning the sleeve that is equipped with the counter-cone while screwing on the nut.

To allow simple, level screwing of the nut onto the collet, on the distal end of the sleeve a non-threaded recess is configured. This recess, which extends the inner diameter of the sleeve, allows the collect to be centered in the nut.

Additional characteristics and advantages of the invention can be seen by referring to the appended sketches, in which an embodiment of the endoscope according to the invention is depicted in exemplary manner.

BRIEF DESCRIPTION OF THE DRAWINGS

FIG. 1 shows a perspective side view of the distal end of an endoscope according to the invention.

FIG. 7 shows a front view of the endoscope with the endoscope head removed.

DETAILED DESCRIPTION OF THE INVENTION

Figure 2:
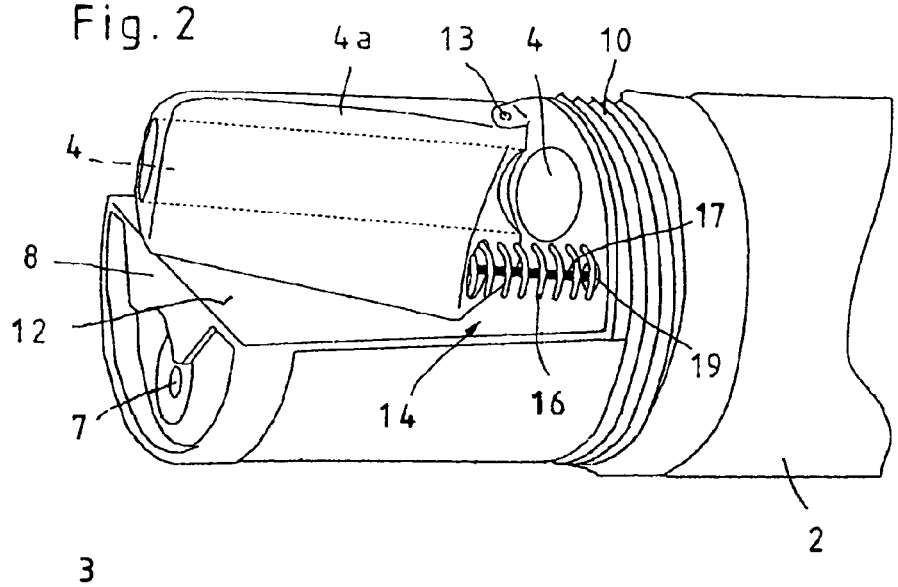
FIG. 2 shows a view as in FIG. 1 but with the endoscope head covering removed.
Figure 6:
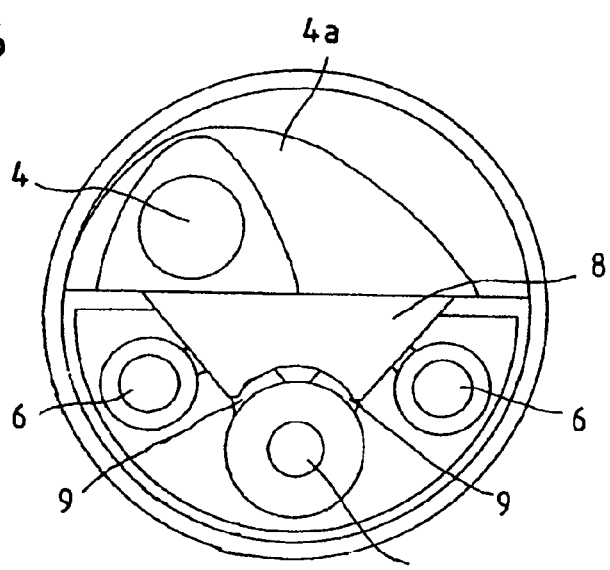
FIG. 6 shows a front view of the drawing in FIG. 2.

In FIG. 1 is seen the distal end of an endoscope 1 having an endoscope head 3 that constitutes the distal end of an endoscope shaft 2 and forms an extension of the endoscope shaft 2.

Inside the shaft 2, as can be seen in FIG. 7, several channels are configured, running in the longitudinal direction, in particular a working channel 4, an irrigation channel 5a, an air channel 5b, and two illumination channels 6. In addition, the lens system 7 of the endoscope 1 extends in the longitudinal direction of the entire shaft 2.

To ensure that the operator working with the endoscope always has a clear view of the surgical area, the rinse water exiting from the irrigation channel 5a is diverted by a duct 8 made of baffle plate onto the lens system 7 and the light systems positioned in the illumination channels 6, so that in the illustrated embodiment the rinse liquid is conducted to the lens system 7 and to the illumination channels 6 by correspondingly positioned conducting channels 9, as seen in particular in FIG. 7. After completion of the lens system rinsing, the irrigation liquid drops are blown away by the air stream emerging from the air channel 5b.

In addition to this drying of the lens system 7, the air stream conducted by the air channel 5b serves to inflate the organs to make it possible thus to insert the endoscope 1 into the examination area with as little friction as possible.

The endoscope head 3 is connected with the endoscope shaft 2 of the endoscope 1 in the illustrated embodiment by a sleeve 11 that can be screwed onto an outer thread 10 of the endoscope head 2 and that at the same time constitutes the outer housing of the endoscope head 3.

Finally, FIG. 2 shows a side view corresponding to FIG. 1, but with the sleeve 1 removed so that the inner structure of the endoscope head 3 is now recognizable. As can be seen from this image as well as from FIG. 3, the endoscope head 3 is constructed as a housing divided in two in the axial direction of the shaft 1 in such a way that the working channel 4 is positioned in the one housing section and the lens system 7, the illumination channels 6 for the lighting systems, and the irrigation channels 5 are positioned in the other housing section.

Figure 4:
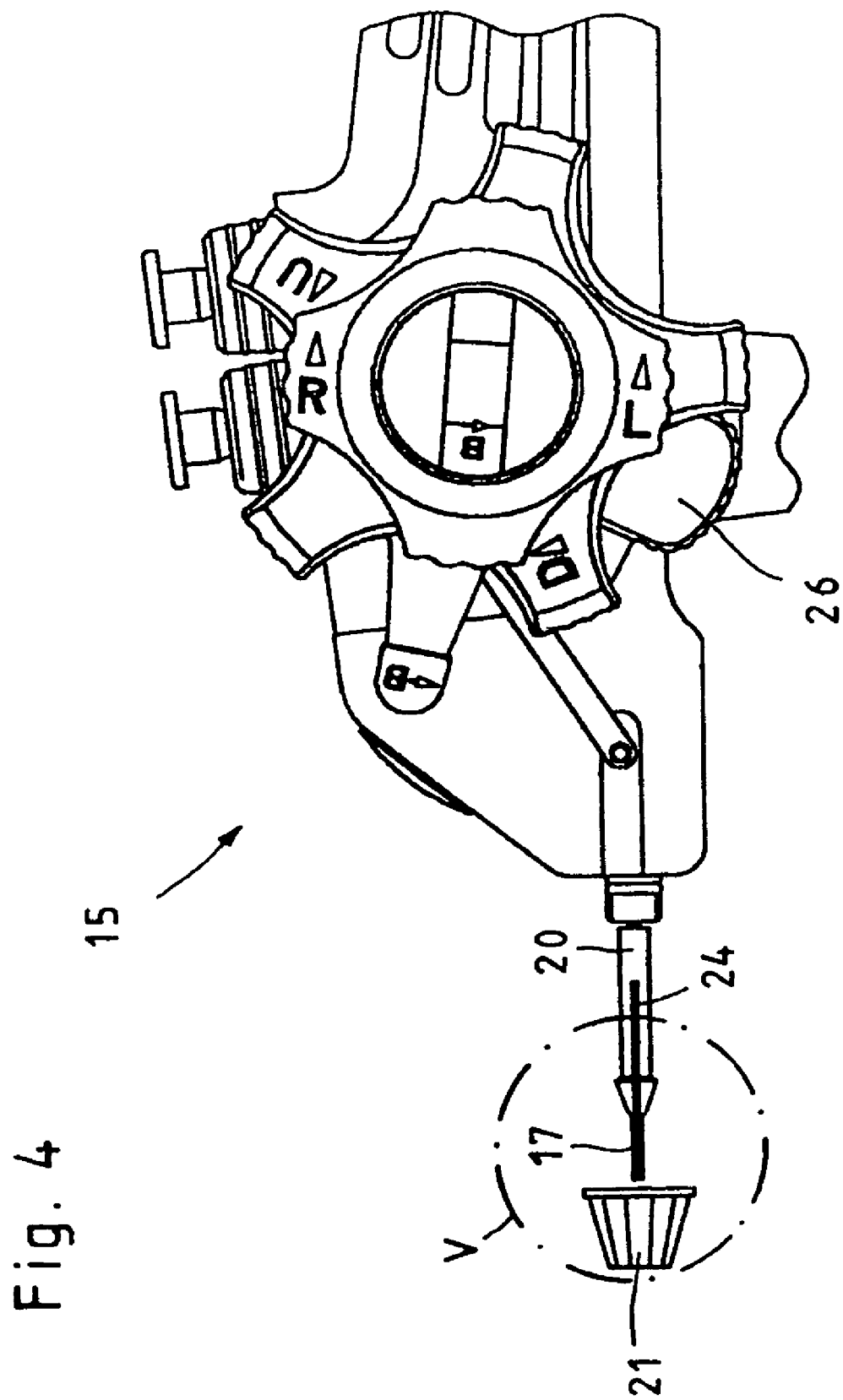
FIG. 4 shows a detailed partial side view of a control handle for an endoscope according to the invention.

The extension of the working channel 4 in the endoscope head 3 has the peculiarity that this part 4a is configured in the shaft 1 so that it can rotate with respect to the related working channel 4 in the plane of the impact plate 12. Because of this ability of the distal part 4a of the working channel 4 to rotate, it is possible to direct a medical instrument, which has been inserted from the proximal end of the endoscope 1 into the working channel 4, accurately to the surgical area. The distal part 4a of the working channel 4 rotates around a pivot axis 13 by means of a Bowden cable 14 that is mounted in the shaft 1 and can be actuated by a control handle 15 on the proximal end of the endoscope 1, as is shown in FIG. 4.

Figure 3:
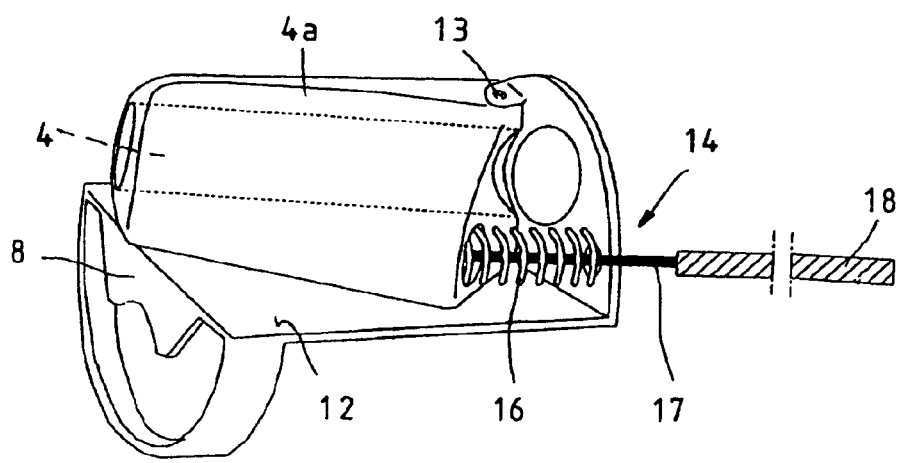
FIG. 3 shows a perspective side view of the endoscope head separated from the endoscope shaft.

As can further be seen from FIGS. 2 and 3, the rotatable part 4a of the working channel 4 is pre-tensioned by a spring element 16 in a starting position in order to have a defined starting position of the working channel 4 from which the movable part 4a can rotate. Because of this starting position it is possible to define a zero point, so that the optical axis constitutes a thoroughly appropriate starting position/zero point position. In order to maintain this starting position also during motion, it is advantageous to provide a stopping device by which the rotatable part 4a of the working channel 4 can be fixed in this starting position.

The Bowden cable is assembled and disassembled on the rotatable part 4a of the working channel 4 and on the control handle 15 as follows:

At the beginning of the installation, a cable cord 17 of the Bowden cable 14 is inserted into a Bowden cable casing 18 and then the Bowden cable casing 18 including the cable cord 17 is introduced from the distal end of the endoscope head 3 into a Bowden cable channel 19 configured in the shaft 1.

Then the endoscope head 3 is secured by the screw-in sleeve 11 on the endoscope shaft 2. The cable cord 7 is pushed into the Bowden cable casing 18 until the cable cord 17 on the proximal end emerges again from the Bowden cable channel 19 in the area of the control handle 15. The cable cord 17 is secured on the proximal end on the control handle 15 by a collet 20 that can be mounted onto the cable cord 17 and is clamped shut by screwing on a nut 21 with the cable cord 17. The rotatable part 4a of the working channel 4 can now be displaced by the control handle 15.

Figure 5:
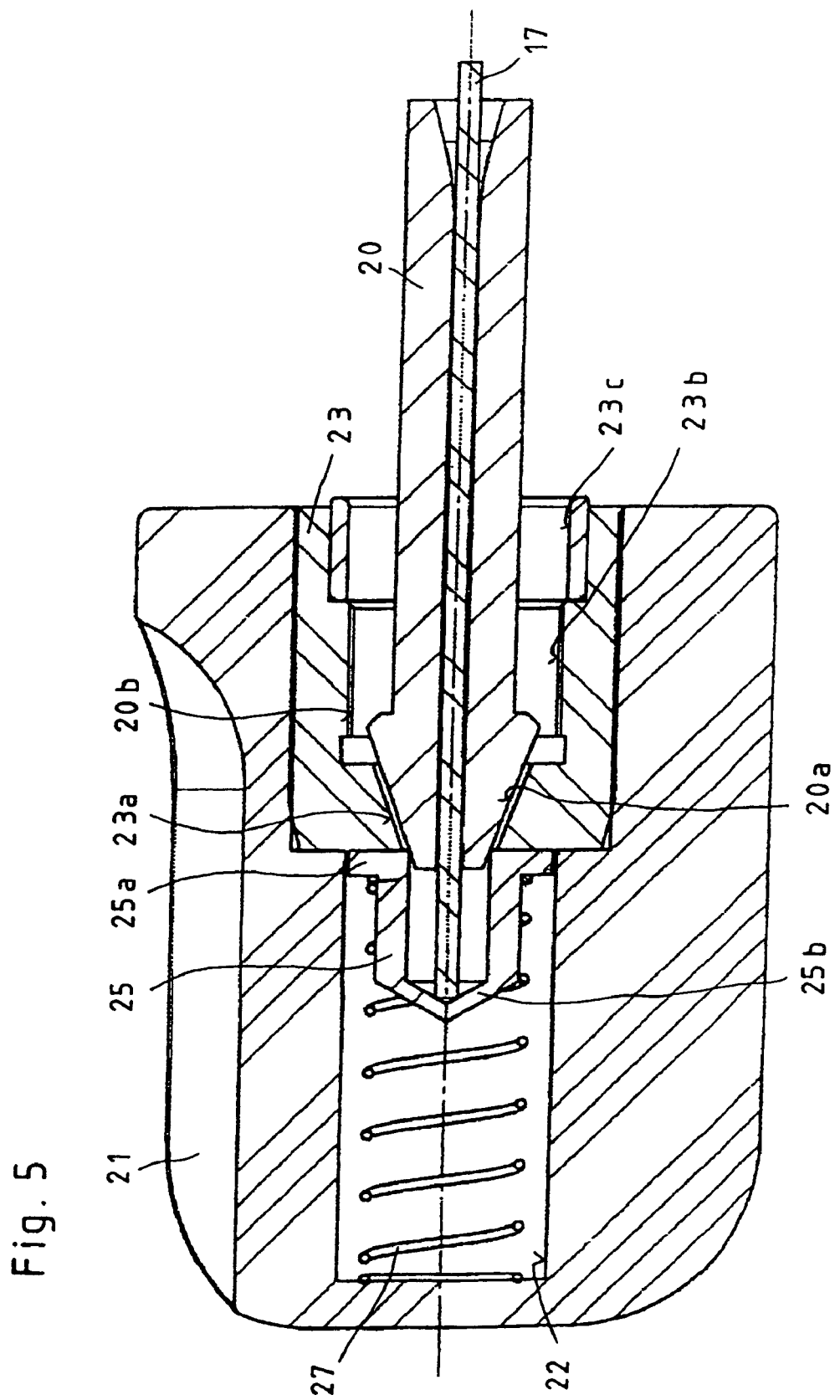
FIG. 5 shows an enlarged cut-out view of detail V from FIG. 4, but in the assembled state.

The structure of the nut 21, configured as a cap nut, and of the collet 20, as well as the manner of tightening the cable cord 17 can be seen from the enlarged detail view in FIG. 5.

As can be seen from the sectional view in FIG. 5, the proximal end of the collet 20, onto which the nut 21 is mounted, is configured as a cone 20a. For insertion of the collet 20, the nut 21 has a pocket hole boring 22, which is inserted essentially flush with the bore hole 22 shutting off a sleeve 23, whose proximal end constitutes a counter-cone 23a to the cone 20a of the collet 20. The depth of insertion of the collet 20 into the sleeve 23 and thus also into the nut 21 is thus limited by the fact that the cone 20a of the collet 20 comes into essentially form-fitting contact on the counter-cone 23a of the sleeve 23. To prevent rotation of the sleeve 23 inside the nut 21 upon screwing the nut 21 onto the collet 20, the sleeve 23 is fixed against rotation in the pocket hole 22 of the nut 21, for instance by cementing.

The nut 21 is secured on the collet 20 by an outer thread 20b that is configured on the collet 20 and engages with an inner thread 23b configured in the sleeve 23. As can be seen from FIG. 5, a non-threaded recess 23c is configured in order to facilitate level screwing of the nut 2 onto the collet 20.

To enable the cable cord 7 to be fixed in the collet 20 by screwing the nut 21 onto the collet 20 and by pressing the counter-cone 23a of the sleeve 23 onto the cone 20a of the collet 20, at least one clamping slit 24 is configured in the collet running in the longitudinal direction of the collet 20, as is shown in FIG. 4. This clamping slit 24 allows a reduction of the diameter of the collet 20 and thus a clamping of the cable cord 17 positioned in the collet 20 when a radially acting force component is exerted on the collet 20.

Perfect actuation of the rotatable part 4a of the working channel 4 by the Bowden cable 14 depends on the correct tightness of the cable cord 17 of the Bowden cable 14. For this purpose it is necessary to ensure that the cable cord 17 is inserted neither too far nor too little into the collet 20 and thus into the nut as well. If the cable cord 17 is inserted too deeply into the collet 20 and thus also into the nut 21, this causes too taut a tightening of the cable cord 17, so that it is barely possible to displace the rotatable part 4a. A similar situation occurs with too weak a tightening of the cable cord 17 because of too short an insertion of the cable cord 17 into the collet 20.

For assembly and disassembly of the collet 20 on the cable cord 17 and/or in the nut 21, the collet 20 can be moved forward and backward in the longitudinal direction by means of a control lever 26 positioned on the control handle 15.

In the embodiment illustrated in FIG. 5, the depth of insertion of the cable cord 17 into the collet 20 is limited by a cap-shaped pressure element 25, which is pre-tensioned by a spring element 27 so that it is contiguous with the sleeve 23 on the proximal end. The spring element 27 here is positioned in the pocket hole 22 of the nut 21 on the proximal end in such a way that the spring element 27 is supported on the distal end on a surrounding collar 25a of the cap-shaped pressure element 25 and on the proximal end on a rear wall of the nut 21, which is configured as a cap nut.

The advantage of this structure is that the cable cord 17 is always held tight in a firmly defined position. This is ensured by the fact that, upon insertion of the collet 20 into the nut 21, the cable cord 17 presses against the pressure element 25, which in turn constantly presses against the cable cord 17 by means of the spring element 27. As can be seen from FIG. 5, a closed rear wall 25b of the cap-shaped pressure element 25 is configured as tapering toward the outside, so that the proximal end of the cable cord 17 inside the pressure element 25 is always positioned exactly centered in the pressure element 25 and the pressure always acts centrally on the cable cord 17. The cable cord 17 is of such dimensions that it is long enough in the starting condition to press against the pressure element 25. As a result of this configuration of the pressure element 25, the possibility of user-caused errors is definitely minimized.

To ensure that the cable cord 17 can be tightened several times with sufficient stability, the cable cord 17 is soldered tightly at the distal end, which is positioned on the rotatable part 4a of the working channel 4.

The endoscope head 3 is disassembled in reverse sequence and begins with the loosening of the nut 2 to release the cable cord 17. Then the sleeve 11 is unscrewed and the endoscope head 3 is withdrawn from the endoscope shaft 2.

An endoscope of this configuration is characterized in that a correct tension of the cable cord 17 of the Bowden cable 17 is always ensured.

What is claimed is:

1. An endoscope having a shaft in which at least one working channel is positioned and having on the distal end of the shaft an endoscope head, such that a part of the working channel contained in the endoscope head can be rotated with respect to the related working channel by a Bowden cable that is mounted on a proximal end of a control handle by a collet, characterized in that a depth of insertion of a cable cord of the Bowden cable into the collet can be limited by a pressure element which is spring-loaded by a single spring element and that is arranged on the control handle in such a way that the pressure element acts on a proximal end of the cable cord and the collet and in that the collet is clamped shut with the cable cord of the Bowden cable by screwing on a nut onto the collet.

2. An endoscope according to claim 1, characterized in that on the collet at the proximal end a cone is configured that engages with a counter-cone configured in a nut that can be screwed onto the collet.

3. An endoscope according to claim 2, characterized in that at least one clamping slit is configured, running in the longitudinal direction of the collet, in the cone of the collet.

4. An endoscope according to claim 2, characterized in that the pressure element is pre-tensioned contiguous to the counter-cone by at least one spring element.

5. An endoscope according to claim 2, characterized in that the counter-cone is configured on a sleeve that can be inserted into the nut.

6. An endoscope according to claim 5, characterized in that the sleeve, can be fixed in the nut so that it cannot rotate.

7. An endoscope according to claim 5, characterized in that the sleeve has a non-threaded recess on the distal end.

8. An endoscope according to claim 1, characterized in that the pressure element takes the form of a cap-shaped component, such that an axial length of the pressure element corresponds to a maximum depth of insertion of the cable cord into the collet.

9. An endoscope according to claim 8, characterized in that a closed rear wall of a cap-shaped pressure element is configured tapering toward an outside.

10. An endoscope according to claim 4, characterized in that the spring element is contiguous with a surrounding collar of a cap-shaped pressure element.

11. An endoscope according to claim 10, characterized in that a distal end of the spring element is supported on a collar of the pressure element and a proximal end of the spring element is supported on a rear wall of the nut that is configured as a cap nut.

12. An endoscope according to claim 6, characterized in that the sleeve can be fixed by cementing in the nut so that it cannot rotate.

* * * * *